United States Patent
Prisco et al.

(10) Patent No.: US 7,741,802 B2
(45) Date of Patent: Jun. 22, 2010

(54) MEDICAL ROBOTIC SYSTEM WITH PROGRAMMABLY CONTROLLED CONSTRAINTS ON ERROR DYNAMICS

(75) Inventors: Giuseppe M. Prisco, Mountain View, CA (US); David J. Rosa, San Jose, CA (US); David. Q Larkin, Menlo Park, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 758 days.

(21) Appl. No.: 11/613,882

(22) Filed: Dec. 20, 2006

(65) Prior Publication Data

US 2007/0151389 A1    Jul. 5, 2007

Related U.S. Application Data

(60) Provisional application No. 60/751,883, filed on Dec. 20, 2005, provisional application No. 60/751,839, filed on Dec. 20, 2005.

(51) Int. Cl.
B25J 9/18 (2006.01)
(52) U.S. Cl. .......................... 318/568.11; 318/568.13; 318/568.18; 318/568.22; 318/632; 74/490.01; 74/490.03
(58) Field of Classification Search ............ 318/568.11, 318/568.12, 568.13, 568.18, 568.2, 568.22, 318/568.23, 632; 700/245, 261; 74/490.01, 74/490.03, 490.05
See application file for complete search history.

(56) References Cited

U.S. PATENT DOCUMENTS 4,772,831 A * 9/1988 Casler et al. ............ 318/568.15
4,851,748 A * 7/1989 Daggett et al. ........... 318/568.2
4,908,556 A * 3/1990 Daggett et al. ........... 318/568.2
4,925,312 A * 5/1990 Onaga et al. ................ 700/261
5,049,796 A * 9/1991 Seraji ....................... 318/568.1

OTHER PUBLICATIONS

Bartolini, G. and E. Punta, "Hybrid second order sliding mode control of constrained manipulators with frictional contact," Proceedings of the 40th IEEE Conference on Decision and Control, Dec. 4-7, 2001, vol. 2, pp. 1398-1403.
Bhat, S.F.; and Bernstein, D.S.; "Continuous finite-time stabilization of the translational and rotational double integrators," IEEE Transactions on Automatic Control, vol. 43, Issue 5, May 1998, pp. 678-682.
Buttolo, Pietro, et al., "Sliding Control of Force Reflecting Teleoperation: Preliminary Studies," Presence, Spring 1994, vol. 3, No. 2, pp. 158-172.
Fiene, J. and G. Niemeyer, "Toward High-Speed Switching Motor Control for Human-Interactive Robotics," Proceedings of the 2005 IEEE International Conference on Robotics and Automation, ICRA 2005. Apr. 18-22, 2005, pp. 1489-1494.
Fridman, L., "The Problem of Chattering: an Averaging Approach," in Variable Structure, Sliding Mode and Nonlinear Control, Lecture Notes in Control and Information Science, No. 247, K.D. Young and U. Ozguner eds., Springer Verlag, 1999, pp. 363-392.

(Continued)

Primary Examiner—Bentsu Ro
Assistant Examiner—Thai Dinh

(57) ABSTRACT

A medical robotic system has a robot arm holding an instrument for performing a medical procedure, and a control system for controlling movement of the arm and its instrument according to user manipulation of a master manipulator. The control system includes at least one joint controller that includes a controller having programmable parameters for setting a steady-state velocity error and a maximum acceleration error for the joint's movement relative to a set point in response to an externally applied and released force.

13 Claims, 6 Drawing Sheets

OTHER PUBLICATIONS

Golo, G. and C. Milosavljevic, "Robust discrete-time chattering free sliding mode control," Systems and Control Letters, vol. 41, No. 1, Sep. 15, 2000, pp. 19-28, pub. by Elsevier.

Guldner, J. and V.I. Utkin, "The chattering problem in sliding mode systems," Proceedings of the 14th International Symposium of Mathematical Theory of Networks and Systems, MTNS 2000, Perpignan, France.

Hung, J.Y., et al., "Variable structure control: a survey," IEEE Transactions on Industrial Electronics, vol. 40, Issue 1, Feb. 1993, pp. 2-22.

Jezernik, K. et al., Observer based sliding mode control of a robotic manipulator. Robotica, 12 (1994); pp. 443-448. Internet: <http://164.8.231.2/projekti/pdf/Robotica_94.pdf>.

Kikuuwe, Ryo and Hideo Fujimoto, Proxy-based Sliding Mode Control for Accurate and Safe Position Control, Proceeding of the 2006 IEEE International Conference on Robotics and Automation, ICRA 2006, Orlando, Florida, May 15-19, 2006, pp. 25-30.

Kwon, D-S., et al., "Design of a teleoperation controller for an underwater manipulator," Proceedings of IEEE International Conference on Robotics and Automation, ICRA'00, Apr. 24-28, 2000, vol. 4, pp. 3114-3119.

Lee, S.-B., et al., "Sliding mode compensation of dry friction," Proceedings of the 1996 IEEE Conference on Control Applications, Sep. 15-18, 1996, pp. 809-813.

Levant, A. and L. Fridman, "Robustness issues of 2-sliding mode control," IEE Control Engineering Series, Pub. Peter Peregrinus Ltd., Great Britain, Issue 66, 2004, pp. 131-156.

Monsees, G. and J.M.A. Scherpen, "Adaptive Switching Gain for a Discrete-Time Sliding Mode Controller," Proceedings of the American Control Conference, Chicago, Illinois, Jun. 28-30, 2000., vol. 3, pp. 1639-1643.

Monsees, Govert, *Discrete-Time Sliding Mode Control*, PhD. Dissertation, Technische Universiteit Delft, 2002.

Newman, W.S., "Robust near time-optimal control," IEEE Transactions on Automatic Control, vol. 35, Issue 7, Jul. 1990, pp. 841-844.

Nguyen, Tri V.M., et al., "A Chattering-Free Variable Structure Controller for Tracking of Robotic Manipulators," Australasian Conference on Robotics and Automation 2003, Internet: <http://www.araa.asn.au/acra/acra2003/papers/02.pdf > 6 pages.

Sabanovic, A., et al., "Chattering free sliding modes in robotic manipulators control," Proceedings of the 1993 IEEE/RSJ International Conference on Intelligent Robots and System—IROS '93, Jul. 26-30, 1993, vol. 2, pp. 1260-1267.

Sane, H.S., et al., "Modified Sliding Mode Control and its Application to Electrostatically Controlled Dual-Axis Micromirrors," Proceedings of the 2004 American Control Conference, Jun. 30-Jul. 2, 2004, vol. 3, pp. 1934-1939.

Shi, J. and Y-S. Lu, "Chatter Free Variable Structure Perturbation Estimator on the Torque Control of Flexible Robot Joints with Disturbance and Parametric Uncertainties," Proceedings of the 1996 IEEE IECON 22nd International Conference on Industrial Electronics, Control, and Instrumentation, Aug. 5-10, 1996, vol. 1, p. 238-243.

Song, G. and R. Mukherjee, "A comparative study of conventional nonsmooth time-invariant and smooth time-varying robust compensators," IEEE Transactions on Control Systems Technology, Jul. 1998, vol. 6, Issue 4, pp. 571-576.

Wang, Jian, et al., "Positioning and Tracking Control of an X-Y Table with Sliding Mode Control," Internet: <http://people.mech.kuleuven.be/~jwang/paper/rocond_2003.pdf> 6 pages.

Vertut, Jean and Coeffet, Philippe Coiffet; "Robot Technology; vol. 3A Teleoperation and Robotics Evolution and Development"; 1986; Prentice-Hall, Inc; Englewood Cliffs, N.J.

\* cited by examiner

MEDICAL ROBOTIC SYSTEM WITH PROGRAMMABLY CONTROLLED CONSTRAINTS ON ERROR DYNAMICS

CROSS REFERENCE TO RELATED APPLICATIONS

This application claims priority to U.S. provisional application Ser. No. 60/751,883 filed Dec. 20, 2005, and U.S. provisional application Ser. No. 60/751,839 also filed Dec. 20, 2005, which are incorporated herein by reference.

FIELD OF THE INVENTION

The present invention generally relates to medical robotic systems and in particular, to a medical robotic system with programmably controlled constraints on error dynamics.

BACKGROUND OF THE INVENTION

Medical robotic systems such as those used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for minimally invasive surgery using such medical robotic systems is strong and growing.

Examples of medical robotic systems include the daVinci® Surgical System and the daVinci® S™ Surgical System from Intuitive Surgical, Inc., of Sunnyvale, Calif. Each of these systems includes a surgeon's console, a patient-side cart, a high performance three-dimensional ("3-D") vision system, and Intuitive Surgical's proprietary EndoWrist™ articulating instruments, which are modeled after the human wrist so that when added to the motions of manipulators holding the surgical instruments, they allow at least six degrees of freedom of motion, which is comparable to or even greater than the natural motions of open surgery.

The daVinci® surgeon's console has a high-resolution stereoscopic video display with two progressive scan cathode ray tubes ("CRTs"). The system offers higher fidelity than polarization, shutter eyeglass, or other techniques. Each eye views a separate CRT presenting the left or right eye perspective, through an objective lens and a series of mirrors. The surgeon sits comfortably and looks into this display throughout surgery, making it an ideal place for the surgeon to display and manipulate 3-D intraoperative imagery.

The patient-side cart typically includes three or more robotic arm assemblies with corresponding slave manipulators for holding and manipulating medical devices such as surgical instruments and image capturing devices for performing and/or viewing a medical procedure at a surgical site within a patient. To manipulate these medical devices, the surgeon's console also includes master input devices which may be selectively associated with the medical devices and their respective slave manipulators. Since the movements of the master input devices and their associated medical devices are scaled, this allows the surgeon to perform intricate medical procedures with greater ease than conventional open surgery. Further, it may even allow the surgeon to perform medical procedures that are not even feasible using conventional open surgery techniques.

To perform a minimally invasive surgical procedure on a patient, one or more incisions are first made in the patient and cannulae inserted therein to gain access to a surgical site within the patient. Setup arms supporting the slave manipulators are then positioned so as to allow the slave manipulators to attach to respective of the cannulae. Surgical instruments engaged on the slave manipulators are then inserted into the cannulae and properly positioned and oriented in order to perform the procedure. A surgeon may then manipulate master manipulators (or master input devices) which are coupled to the slave manipulators and their respective surgical instruments through one or more controllers to perform the surgical procedure.

The initial positioning and orientating of the surgical instruments at the surgical site is generally performed by an assistant who is positioned next to the patient and manually moves their respective slave manipulators so as to move the surgical instruments into their proper positions and orientations at the surgical site. Typically such positioning and orientating involves a two-step procedure in which, in a first part, each slave manipulator is attached to its assigned cannula and its surgical instrument engaged on it, and in a second part, the slave manipulator is manipulated so that its surgical instrument is properly positioned and oriented at the surgical site to perform its role in the minimally invasive surgical procedure. Although described as a two-part procedure for each slave manipulator, it is to be appreciated that the assistant may perform both parts concurrently or otherwise in an overlapping fashion, as well as sequentially so as to be performed one after the other.

To perform the first part of the initial positioning of a surgical instrument, the assistant depresses a first release button on a slave manipulator, which releases brakes holding setup joints of its corresponding setup arm in place so as to allow movement of the slave manipulator. The positioning of the slave manipulator is conventionally facilitated by the use of gravity-balanced or non-gravity loaded setup joints. After the slave manipulator is positioned so that it can be attached to its assigned cannula and is attached to it, the assistant may then stop depressing the first release button, which causes the brakes to hold their corresponding setup joints in place, thus locking the translational position of the cannula attached to the slave manipulator at this point. Additional details in performing this part of the procedure and the general construction of slave manipulators and their setup arms as pertaining to such procedure are provided in commonly owned U.S. Pat. No. 6,246,200 entitled "Manipulator Positioning Linkage for Robotic Surgery," which is incorporated herein by this reference.

To perform the second part of the initial positioning of the surgical instrument, the assistant engages the surgical instrument onto the slave manipulator so that it is capable of inserting it into the cannula, pivoting the instrument around a pivot point located at the surgical port of the cannula, and driving an end effector at the distal end of the surgical instrument with degrees of freedom resembling wrist motion. It may be noted at this point that the surgical instrument tip is inside the cannula and thus, is no longer visible to the assistant since it is now shielded by the anatomy.

To proceed, the assistant depresses a second button on or proximate to its slave manipulator, which disengages active joints of the slave manipulator from being controlled by their associated master manipulator. This allows the assistant to freely move the slave manipulator to insert the surgical instrument into its cannula and pivot about it about the incision so as to point in the proper direction and at the proper distance into the incision. If an endoscope has been previously positioned in the patient to view the surgical site, typically this step is performed while the assistant views the image of the surgical site provided by the endoscope. After the surgical instrument is thus positioned at the surgical site, the assistant may then stop depressing the second button, which allows the surgeon to re-engage control of the active joints of the slave manipulator through the master manipulator so that the surgeon may perform the surgical procedure by manipulating the master manipulator. To facilitate the positioning tasks described above, the first and second buttons may be effective only while they are depressed (and thus work as momentary buttons) or they can remain effective after they are released until they are depressed again (and thus work as toggle buttons).

To facilitate easy movement of the slave manipulator during the second part of the positioning procedure, the slave manipulator may be mechanically gravity balanced using, for example, counter balance weights, so as to significantly reduce gravity effects and consequently, the force necessary for a person to physically move the slave manipulator. Additionally, the slave manipulator may be designed so as to have very high mechanical efficiency so that the friction does not change much with the force applied to the manipulator, have low friction forces or torque to overcome when moving the manipulator, and have low mass or inertia so that the manipulator may be accelerated with low force or torque.

Although a slave manipulator that does not have all of these mechanical characteristics may not be easy to manually position quickly and accurately, it may be advantageous to give away some of these mechanical characteristics in exchange for other benefits such as larger workspace, smaller footprint, or a lighter slave manipulator. In such a design, a control system that is capable of recovering the lighter feeling of the mechanically gravity balanced design is desirable.

One way of recovering the lighter feeling provided by counterweights while manually moving the slave manipulator is to use joint motor torques to exert assisting forces to effectively balance the gravitational weight of the slave manipulator. Using this approach, the joint motors of the slave manipulator are generally capable of applying torques greater than those necessary for normal control activities. Consequently, when the control of the slave manipulator is optimized for tracking purposes (i.e., to follow its corresponding master input device), for instance by the adoption of large control gains, the slave manipulator may be difficult to backdrive (i.e., cause its associated master input device to follow externally applied movement of the slave manipulator). Also, when the control of the slave manipulator is optimized for tracking purposes, it may tend to spring back quickly and overshoot its commanded position after it has been temporarily displaced by a large amount away from its commanded position by an externally applied force. Each of these characteristics tends to make the slave manipulator human unfriendly to the assistant during setup and to the patient during the performance of a medical procedure.

OBJECTS AND SUMMARY OF THE INVENTION

Accordingly, one object of aspects of the present invention is a joint controller and method implemented in the joint controller for controlling a joint in a medical robotic system which provides optimal tracking performance while limiting unsafe forces exerted by an associated slave manipulator against its environment.

This and additional objects are accomplished by the various aspects of the present invention, wherein briefly stated, one aspect is a medical robotic system comprising: a manipulator having a motor driven joint for moving the manipulator; and a processor configured to control movement of the joint from a current position to a target position according to a control law from which a motor joint command may be determined using joint feedback and feedforward motor torque terms, wherein the joint feedback motor torque term is computed as a function of at least a position error computed as a difference of the current and target positions, the feedforward joint motor torque term is computed as a function of the joint target position, the feedback motor torque term is limited to a first programmable limit value, and the feedforward motor torque term is limited to a maximum motor torque value.

Another aspect is a medical robotic system comprising: a manipulator having a motor driven joint for moving the manipulator; and a processor configured to control movement of the joint from a current position to a target position according to a feedback control law that computes the motor joint command as a function of the difference between the current position and the target position and as a function of the difference between a current velocity and target velocity, while preventing the current velocity error of the joint movement to exceed in absolute value a programmable maximum velocity value.

Another aspect is a method for controlling movement of a motor driven joint of a manipulator, comprising: controlling movement of the joint from a current position to a target position according to a feedback control law that computes the motor joint command as a function of the difference between the current position and the target position and as a function of the difference between a current velocity and target velocity, while preventing the current velocity error of the joint movement to exceed in absolute value a programmable maximum velocity value.

Additional objects, features and advantages of the various aspects of the present invention will become apparent from the following description of its preferred embodiment, which description should be taken in conjunction with the accompanying drawings.

DETAILED DESCRIPTION OF THE PREFERRED EMBODIMENT

Figure 1:
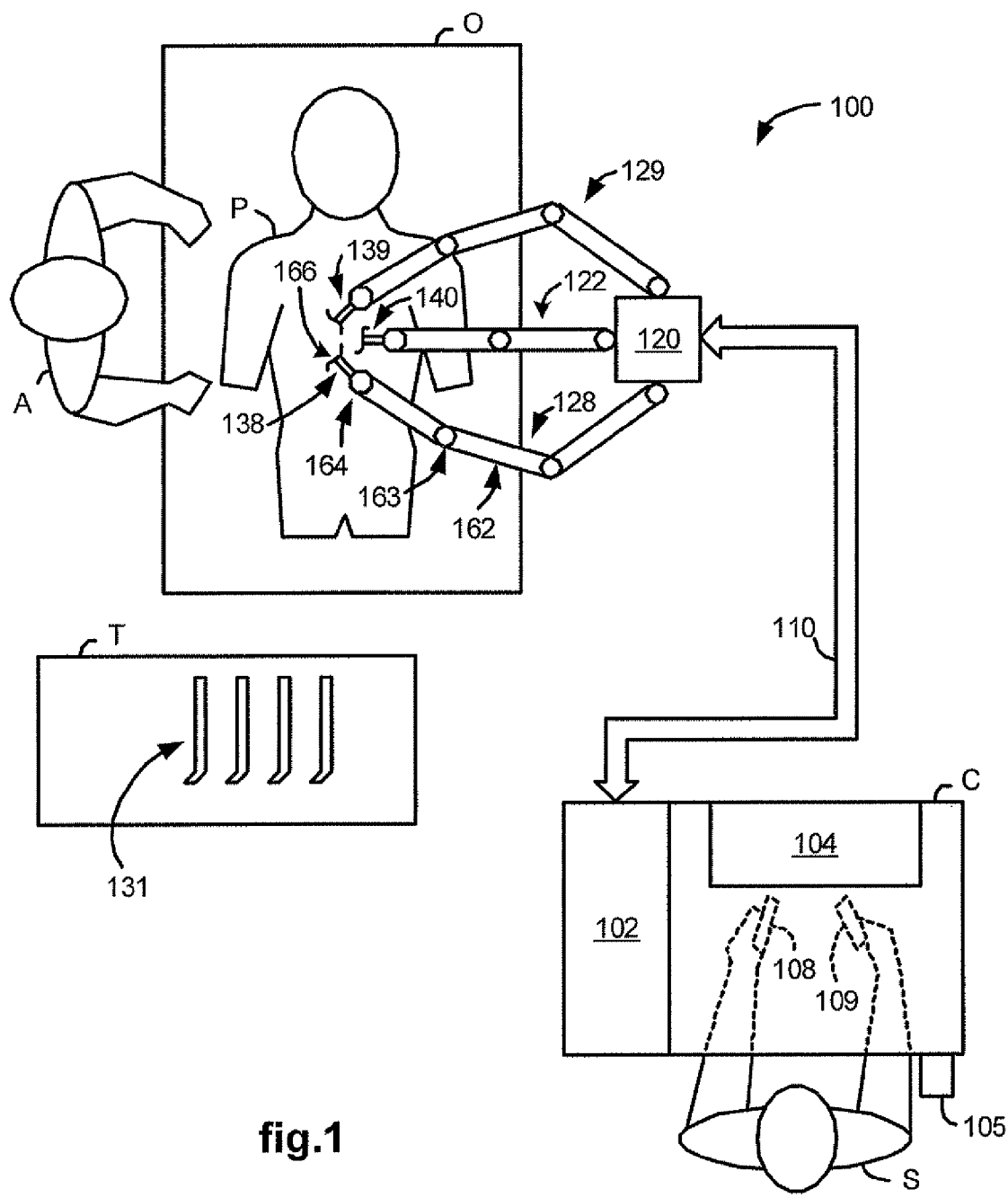
FIG. 1 illustrates a top view of an operating room employing a medical robotic system utilizing aspects of the present invention.

FIG. 1 illustrates, as an example, a top view of an operating room employing a medical robotic system. The medical robotic system in this case is a minimally invasive robotic surgical system 100 including a Console ("C") utilized by a Surgeon ("S") while performing a medical procedure, such as a diagnostic or surgical procedure, with assistance from one or more Assistants ("A"), on a Patient ("P") who is reclining on an Operating table ("O").

The Console includes a 3-D monitor 104 for displaying a 3-D image of a surgical site to the Surgeon, left and right manipulatable control devices 108, 109, a foot pedal 105, and a processor 102. The control devices 108, 109 may include any one or more of a variety of input devices such as joysticks, gloves, trigger-guns, hand-operated controllers, or the like. The processor 102 may be a dedicated computer integrated into the Console or positioned next or near to it, or it may be broken up into a number of processing or controller components that are distributed in a distributed processing fashion throughout the System 100.

The Surgeon performs a medical procedure by manipulating the control devices 108, 109 (also referred to herein as "master manipulators" and "master input devices") so that the processor 102 causes slave manipulators of their respectively associated robotic arm assemblies 128, 129 to manipulate their respective removably coupled surgical instruments 138, 139 (also referred to herein as "tools") accordingly, while the Surgeon views the surgical site in 3-D on the Console monitor 104 as it is captured by a stereoscopic endoscope 140.

Each of the tools 138, 139, as well as the Endoscope 140, is conventionally inserted through a tool guide (not shown) into the Patient so as to extend down to the surgical site through a corresponding minimally invasive incision such as Incision 166. The number of surgical tools used at one time and consequently, the number of robotic arms being used in the system 100 will generally depend on the medical procedure being performed and the space constraints within the operating rooms among other factors. If it is necessary to change a tool being used during a procedure, the Assistant may remove the tool no longer being used from its robotic arm assembly, and replace it with another tool 131 from a Tray ("T") in the operating room.

Each of the robotic arm assemblies 122, 128, 129 includes a slave manipulator and setup arms. The slave manipulators are robotically moved using motor controlled joints (also referred to herein as "active joints") in order to manipulate and/or move their respectively held medical devices. The setup arms may be manually manipulated by releasing normally braked joints (also referred to herein as "setup joints") to horizontally and vertically position the robotic arm assemblies 122, 128, 129 so that their respective medical devices may be inserted into their respective tool guides.

Preferably, the monitor 104 is positioned near the Surgeon's hands so that it will display a projected image that is oriented so that the Surgeon feels that he or she is actually looking directly down onto the operating site. To that end, images of the tools 138, 139 preferably appear to be located substantially where the Surgeon's hands are located.

The processor 102 performs various functions in the system 100. One important function that it performs is to translate and transfer the mechanical motion of control devices 108, 109 to their respective slave manipulators of robotic arm assemblies 128, 129 through control signals over bus 110 so that the Surgeon can effectively manipulate their respective tools 138, 139. Another important function is to implement various control system processes as described herein.

Although described as a processor, it is to be appreciated that the processor 102 may be implemented in practice by any combination of hardware, software and firmware. Also, its functions as described herein may be performed by one unit, or divided up among different components, each of which may be implemented in turn by any combination of hardware, software and firmware.

For additional details on the construction and operation of medical robotic systems such as described herein, see, e.g., commonly owned U.S. Pat. No. 6,493,608 "Aspects of a Control System of a Minimally Invasive Surgical Apparatus," and commonly owned U.S. Pat. No. 6,424,885 "Camera Referenced Control in a Minimally Invasive Surgical Apparatus," which are incorporated herein by reference.

Figure 2:
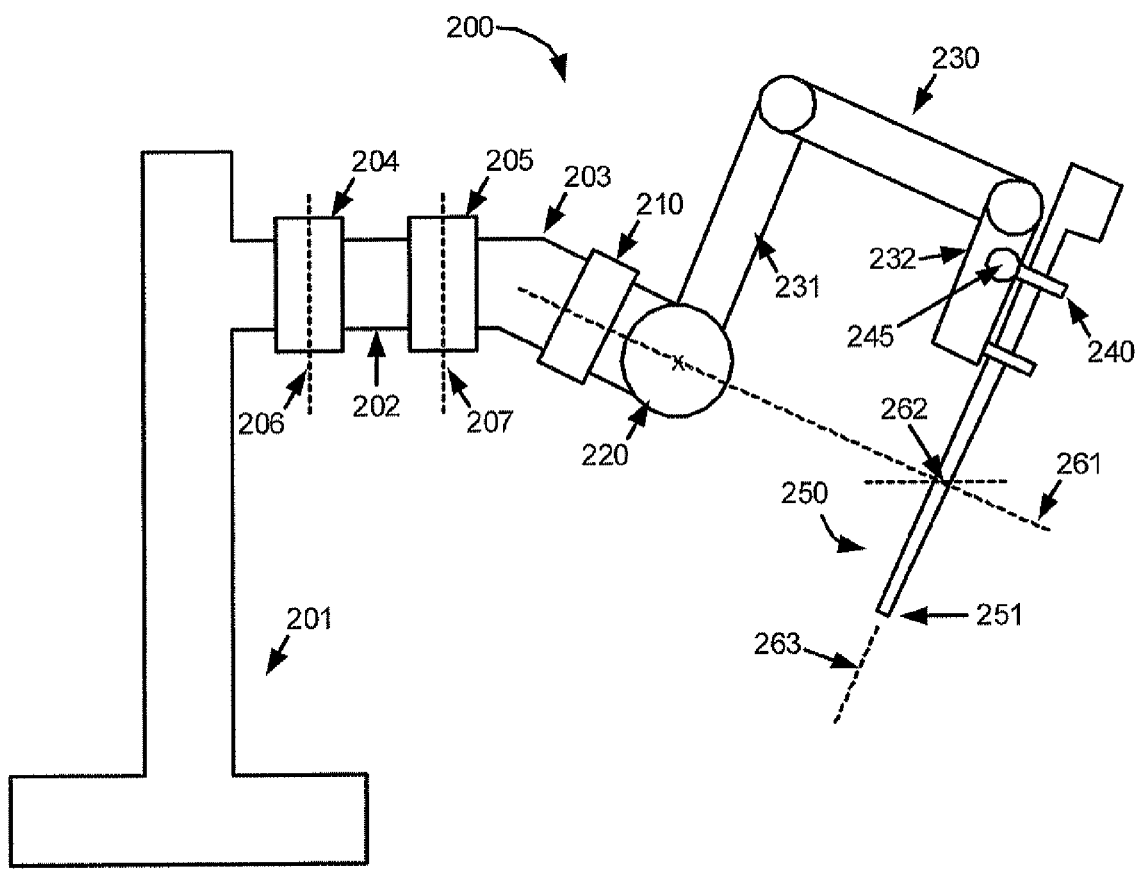
FIG. 2 illustrates a simplified side view of a robotic arm assembly that is usable with various aspects of the present invention.

FIG. 2 illustrates, as an example, a side view of a simplified (not necessarily in proportion or complete) robotic arm assembly 200 (which is representative of the robotic arm assemblies 128, 129) holding a surgical instrument 250 (which is representative of tools 138, 139) for performing a medical procedure. The surgical instrument 250 is removably held in tool holder 240. The robotic arm assembly 200 is mechanically supported by a base 201, which may be part of a patient-side movable cart or affixed to the operating table or ceiling. It includes links 202, 203 which are coupled together and to the base 201 through horizontal setup joints 204, 205.

The setup joints 204, 205 in this example are passive joints that allow manual positioning of the arm 200 when their brakes are released. For example, setup joint 204 allows link 202 to be manually rotated about axis 206, and setup joint 205 allows link 203 to be manually rotated about axis 207. The setup arm or portion of the robotic arm assembly 200 includes these setup joints.

Although only two links and two setup joints are shown in this example, more or less of each may be used as appropriate in this and other robotic arm assemblies in conjunction with the present invention. For example, although setup joints 204, 205 are useful for horizontal positioning of the arm 200, additional setup joints may be included and useful for limited vertical and angular positioning of the arm 200. For major vertical positioning of the arm 200, however, the arm 200 may also be slidably moved along the vertical axis of the base 201 and locked in position.

The robotic arm assembly 200 also includes three active joints driven by motors. A yaw joint 210 allows arm section 230 to rotate around an axis 261, and a pitch joint 220 allows arm section 230 to rotate about an axis perpendicular to that of axis 261 and orthogonal to the plane of the drawing. The slave manipulator of the robotic arm assembly 200 includes these active joints.

The arm section 230 is configured so that sections 231, 232 are always parallel to each other as the pitch joint 220 is rotated by its motor. As a consequence, the instrument 250 may be controllably moved by driving the yaw and pitch motors so as to pivot about the pivot point 262, which is generally located through manual positioning of the setup joints 204, 205 so as to be at the point of incision into the patient. In addition, an insertion gear 245 may be coupled to a linear drive mechanism (not shown) to extend or retract the instrument 250 along its axis 263.

Although each of the yaw, pitch and insertion joints or gears, 210, 220, 245, is controlled by an individual joint or gear controller, the three controllers are controlled by a common master/slave control system so that the slave manipulator of the robotic arm assembly 200 may be controlled through user (e.g., surgeon) manipulation of its associated master manipulator.

Figure 3:
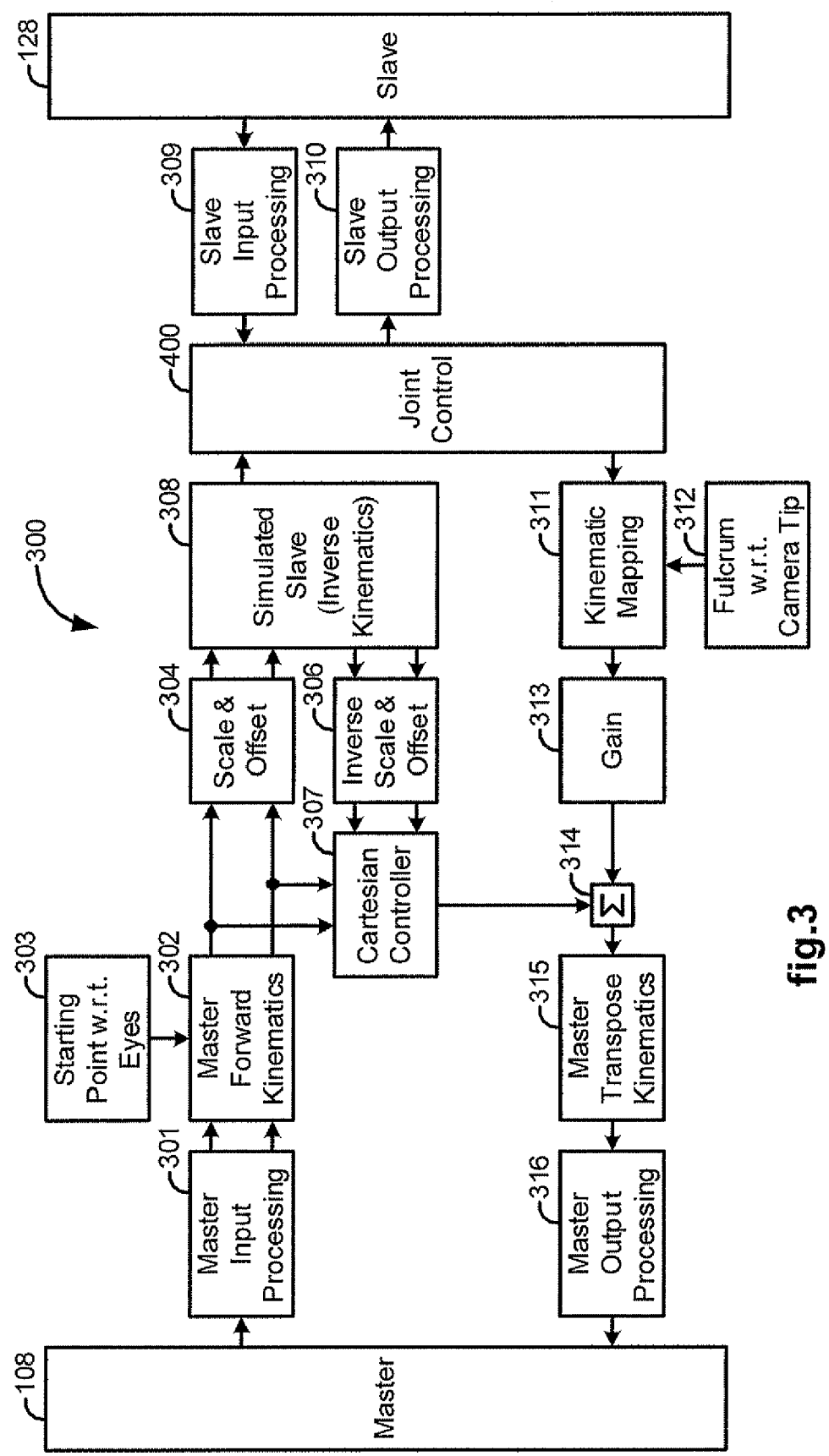
FIG. 3 illustrates a block diagram of a master/slave control system utilizing aspects of the present invention.

FIG. 3 illustrates, as an example, a block diagram of a master/slave control system 300 for controlling movement of the slave manipulator of the robotic arm assembly 128 and consequently, the position and orientation of its attached tool 138, as commanded by movement of the master manipulator 108 by a surgeon. A similar control system may also be provided for the slave manipulator of the robotic arm assembly 129 and its associated master manipulator 109.

Both the master and slave manipulators include a number of linkages connected by joints so as to facilitate multiple degrees-of-freedom movement. As the surgeon moves the master manipulator 108 from one position to another during the course of performing a surgical procedure, sensors associated with the master manipulator joints provide information indicating such command movement in master joint space, and sensors associated with the slave manipulator joints provide information indicating slave manipulator and consequently, tool 138 movement in slave joint space for feedback purposes. In order to better detect and control fine movements of their respective joints (e.g., in the target velocity range of 0.0005 to 0.01 radians per second at the joint, including the motion during the transition from zero velocity to the velocity in the target range), high resolution encoders are preferably used for the joint sensors.

A master input processing unit 301 receives the information of the master joint positions, which are sampled at the control system processing rate (e.g., 1300 Hz in the present example), from the master joint sensors in the master manipulator 108, and computes joint velocities from the sensed joint positions. A master forward kinematics processing unit 302 receives the master joint positions and velocities from the master input processing unit 301, transforms them from master joint space to corresponding positions and velocities of the master frame (i.e., the frame associated with the master manipulator 108) in Cartesian space relative to the eye reference frame (i.e., the reference frame associated with the position of the surgeon's eyes), using, for example, a Jacobian matrix and eye related information separately determined and provided in block 303.

A scale and offset processing unit 304 receives the Cartesian position and velocity commands from the master forward kinematics processing unit 302, scales the commanded movement according to a scale factor selected to perform the surgical procedure, and takes into account offsets to generate desired slave tool frame (i.e., the frame associated with the tool 138) positions and velocities. The scale adjustment is useful where small movements of the slave manipulator of the robotic arm assembly 128 are desired relative to larger movement of the master manipulator 108 in order to allow more precise movement of the slave tool 138 at the surgical site. The offsets, on the other hand, determine, for example, the corresponding position and/or orientation of an end effector frame (e.g., the frame associated with an end effector of the tool 138) in the camera reference frame (i.e., the frame associated with the distal tip of the endoscope 140) relative to a position and orientation of the master frame in the eye reference frame.

A simulated slave processing unit 308 receives desired slave tool frame position and velocity commands from the scale and offset processing unit 304, and limits the desired slave tool frame position, orientation and velocities, to assigned Cartesian Limits for instance to enforce correct and intuitive operation of the tool 138 by keeping it within its dexterous workspace. The simulated slave processing unit 308 generates simulated slave joint positions and velocities corresponding to the limited slave tool frame positions and velocities, while making sure that the generated slave joint's positions and velocities do not exceed the actual slave joint's range of motion and maximum velocities (i.e., joint limits) even in the vicinity of kinematic singularities for the slave kinematics.

An inverse scale and offset processing unit 306 receives the simulated joint position and velocity commands from the simulated slave processing unit 308, and performs an inverse function to that of the scale and offset processing unit 304 on them. A Cartesian controller 307 receives as first inputs, the inputs to the scale and offset processing unit 304 and as second inputs, the outputs of the inverse scale and offset processing unit 306. The Cartesian controller 307 then generates an error signal as a difference of the first and second inputs, and a Cartesian force "$F_{CART}$" from the error signal such as with the following formula:

$$F_{CART} = K(\Delta x) + B(\Delta \dot{x}) \quad (1)$$

where "K" is a spring constant, "B" is a damping constant, "$\Delta \dot{x}$" is the difference between the Cartesian velocity inputs to the Cartesian controller 307 and "$\Delta x$" is the difference between the Cartesian position inputs to the Cartesian controller 307. For an orientation error, a corresponding torque in Cartesian space is determined.

A master transpose kinematics processing unit 315 receives the Cartesian force $F_{CART}$ through a summation node 314, and generates a corresponding torque in joint space using, for example, the Jacobian transpose matrix and kinematic relationships associated with the master manipulator 108. A master output processing unit 316 receives the master torque signals from the master transpose kinematics processing unit 315, generates electrical currents corresponding to the master torque signals, and supplies the electrical currents to corresponding master joint motors of the master manipulator 108. As a result, a surgeon operating the master manipulator 108 feels the Cartesian force, $F_{CART}$, whenever the surgeon is commanding a position or velocity which exceeds system Cartesian or slave joint limits, or would result in a kinematic singularity condition for the slave manipulator of the robotic arm assembly 128.

As the master input processing unit 301 is receiving master joint positions from sensors in the master manipulator 108, a slave input processing unit 309 is also receiving slave joint positions from position sensors in the slave manipulator at the control system processing rate. A joint control unit 400 receives the slave joint positions from the slave input processing unit 309 and the simulated joint position commands provided from the simulated slave processing unit 308, and generates slave torque command signals for the slave joint motors and master torque feedback command signals for the master joint motors.

The slave torque command signals are generated by the joint control unit 400 so as to drive joints of the slave manipulator until feedback errors calculated in the joint control unit 400 zero out. A slave output processing unit 310 receives the slave torque command signals from the joint control unit 400, converts them into appropriate electrical currents, and supplies the electrical currents to the joint motors of the slave manipulator so as to drive the motors accordingly.

The master torque feedback command signals are generated by the joint control unit 400 as a function of the slave joint position and velocity tracking errors so as to reflect forces being exerted against the tool 138 or its slave manipulator back to the master manipulator 108 so that they may be felt by the surgeon. A kinematic mapping unit 311 receives the master torque feedback command signals from the joint control unit 400, and generates the corresponding Cartesian force at the tip of the tool 138 relative to the camera frame of the endoscope 140 using the slave kinematic configuration and the previously calculated slave fulcrum (e.g., pivot point) position information provided in block 312.

A gain 313 adjusts the magnitude of the Cartesian force so as to ensure system stability while providing adequate force sensation to the surgeon. The gain adjusted Cartesian force is then passed through the summation node 314, and processed along with the Cartesian force provided by the Cartesian controller 307 through the Master transpose kinematics processing unit 315 and Master output processing 316 as previously described in reference to their processing of the Cartesian force provided by the Cartesian controller 307.

Additional details related to conventional aspects of the master/slave control system 300, such as the various reference frames referred to herein and the calculation of the surgeon eye related information provided in block 303 and the slave fulcrum information provided in block 312, which are based upon well-known mathematics, are described, for example, in previously incorporated by reference and commonly owned U.S. Pat. No. 6,424,885, "Camera Referenced Control in a Minimally Invasive Surgical Apparatus."

The joint control unit 400 includes a joint controller for each active joint and gear of the slave manipulator of the robotic arm assembly 128 that is being controlled by the master/slave control system 300. In particular, where the slave manipulator 128 includes a yaw joint 210, a pitch joint 220, and an insertion axis gear 245, such as the robotic arm assembly 200 of FIG. 2, each of these joints or gears will have its own controller.

Figure 4:
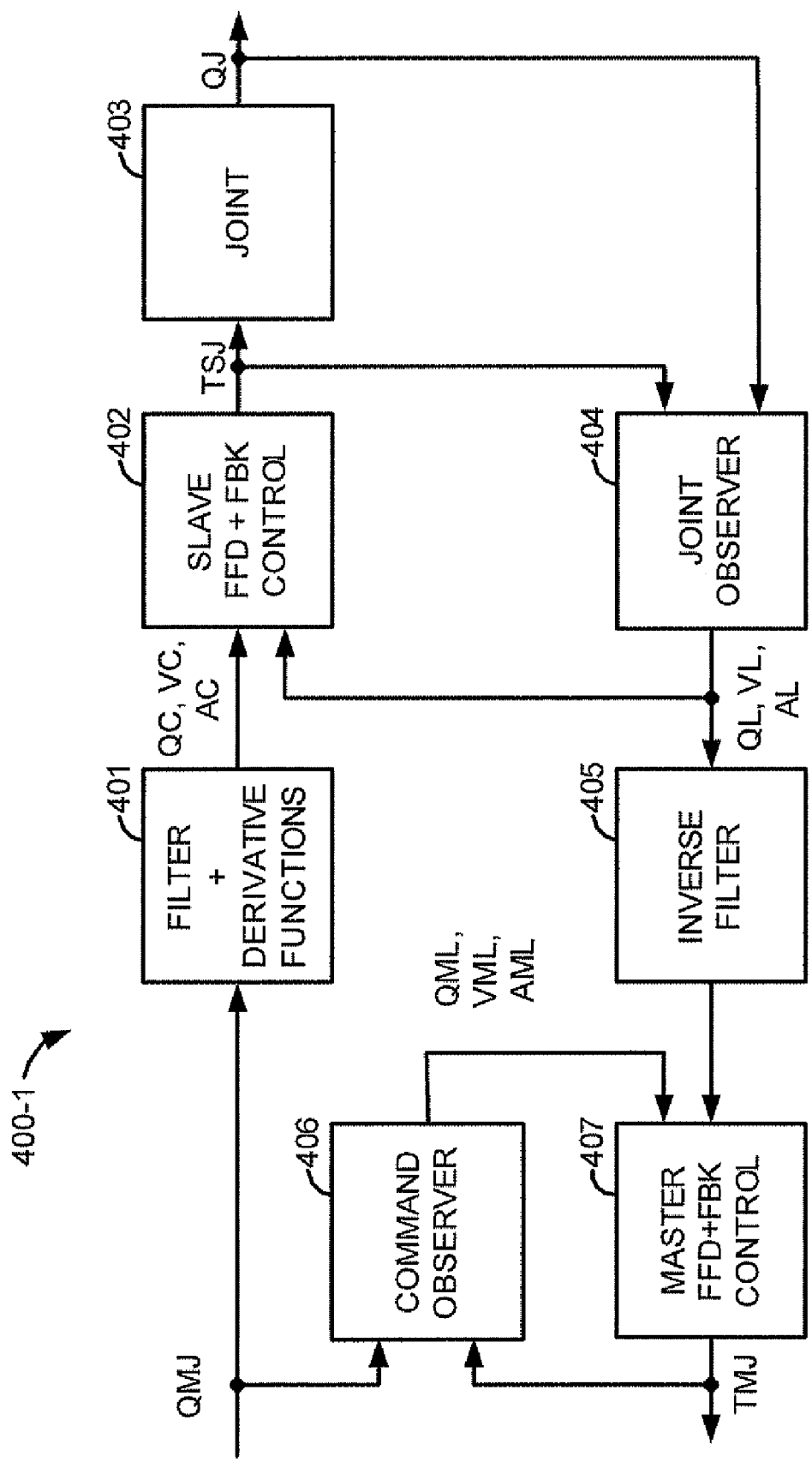
FIG. 4 illustrates a block diagram of a slave joint controller utilizing aspects of the present invention.

FIG. 4 illustrates, as an example, a block diagram of one such joint controller 400-1 (e.g., for controlling movement of either the yaw, pitch, or insertion joint or gear, 210, 220, 245, of the robotic arm assembly 200). To simplify the description herein and in the claims, the term "joint" is to be understood to include gears as well as any other controllable component coupled to linear drive mechanisms that may be used in controlling robotic arm assemblies.

First, an appropriate filter (plus derivative functions S and $S^2$) 401 is introduced into a forward path of the joint controller 400-1. The derivative functions are included, because the joint controller 400-1 employs a slave feedforward ("FFD") and feedback ("FBK") controller 402, which requires joint velocity and acceleration commands, as well as a joint position command. In order to better control fine movements of the joint, the controller 402 is preferably implemented so as to include a sliding mode controller, as described below. The filter used in block 401 is preferably a linear filter. The derivatives of a joint position command QMJ provided to the block 401 may be calculated after filtering of the joint position command QMJ, or they may be calculated before filtering of the joint position command QMJ. In the latter case, each of the joint position, velocity and acceleration commands may be individually filtered using the same or different filters. Preferably, the block 401 (i.e., the filter+derivative functions) is a digital state space balanced realization using standard techniques for its conversion from the continuous domain to the digital domain (e.g., Tustin method, Euler method, etc.). The joint position command QMJ is one of the simulated joint position commands from the simulated slave processing unit 308. The filtered joint position, velocity and acceleration commands QC, VC and AC are then provided to the slave controller 402.

Since the filter in block 401 inserts delay into the joint controller 400-1, an inverse filter 405 is inserted in a feedback path to the master manipulator 108 to at least partially compensate for that delay. The inverse filter 405 is also preferably implemented in state space. In order to be the inverse of the forward path filter, it is configured so as to have a reciprocal transfer function. Thus, it is characterized as amplifying its incoming signal starting at the same cut-off frequency as the forward path filter so as to add phase lead instead of lag. Additional details on the construction and operation of such filters are described in commonly owned U.S. patent application Ser. No. 11/509,172 entitled "Robotic Surgical System with Joint Motion Controller Adapted to Reduce Instrument Tip Vibrations," filed Aug. 24, 2006, which is incorporated herein by this reference, To further enhance the accuracy (by reducing noise) and stability (by reducing loop delays) of the joint controller 400-1 and/or master/slave control system 300, a joint observer 404 is preferably inserted so as to estimate actual joint positions, velocities and accelerations, QL, VL and AL, using sensed position indications QJ from an encoder or sensor coupled to the slave joint, and torque commands TSJ provided to drive the slave joint motor. The slave joint motor, slave joint, and slave joint sensor are all included and indicated in this example by reference number 403. Note that the outputs of the joint observer 404 are provided to the inverse filter 405 and the slave controller 402 so that differences between corresponding of the joint position QC, velocity VC and acceleration AC commands, and estimated joint position QL, velocity VL and acceleration AL may be computed by the slave controller 402 in generating the torque command signal TSJ.

Also, to further enhance the accuracy and stability of the joint controller 400-1 and/or master/slave control system 300, a command observer 406 is preferably inserted so as to estimate joint position QML, velocity VML and acceleration AML commands using the joint position command QMJ and a torque feedback command TMJ. Note that the outputs of the command observer 406 are provided as negative values to the master controller 407 along with the outputs of the inverse filter 405, so that differences between corresponding of the inverse filtered, estimated joint positions QL, velocities VL and accelerations AL, and estimated joint position QML, velocity VML and acceleration AML commands may be calculated and used by the master controller 407 in generating the feedback torque TMJ.

Figure 5:
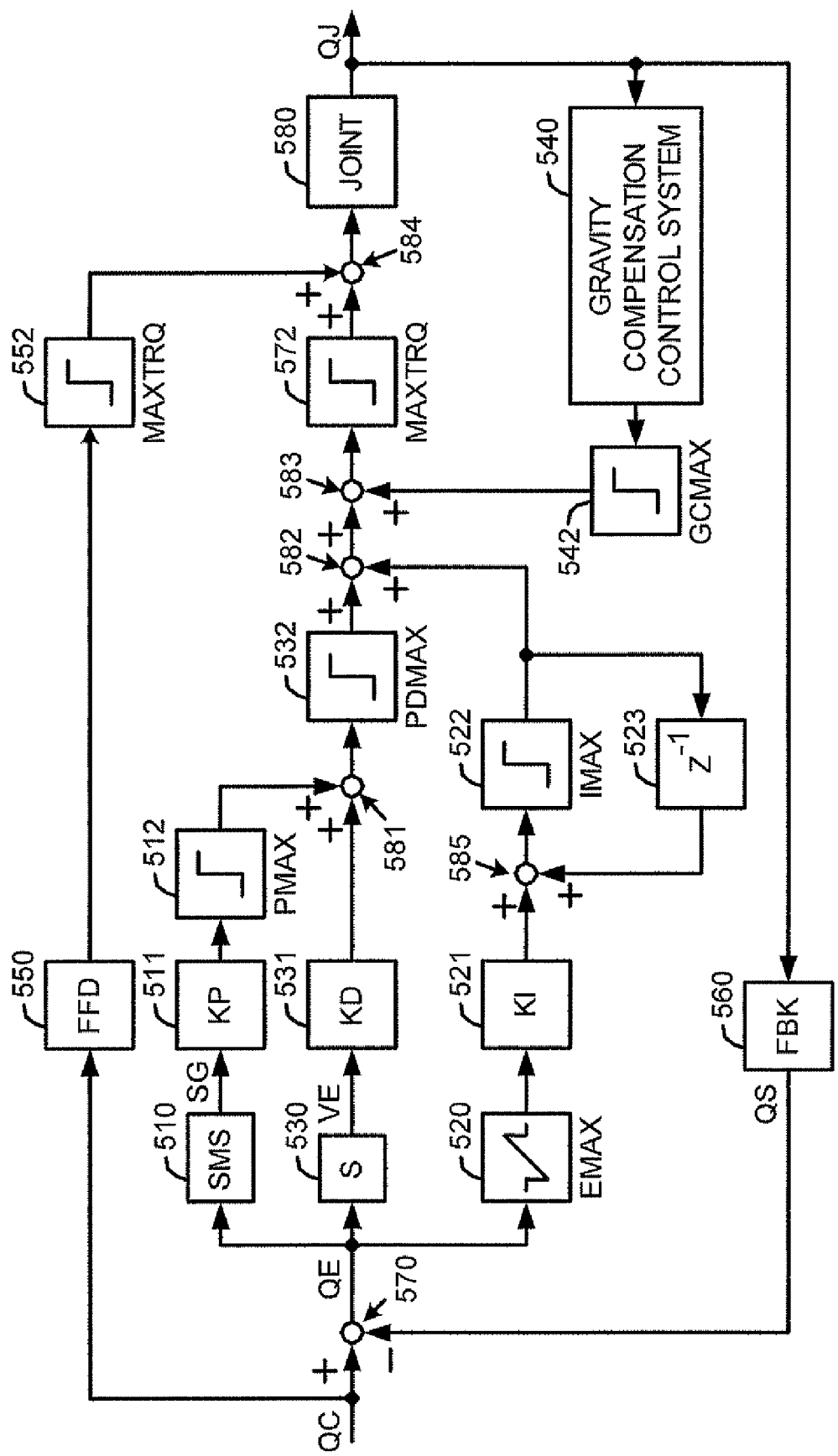
FIG. 5 illustrates a block diagram of a slave feedforward and feedback controller with gravity compensation, utilizing aspects of the present invention.

FIG. 5 illustrates, as an example, a block diagram of a slave feedforward and feedback controller with gravity compensation. In this example, only the position command QC and feedback QS are shown to simply the description. The velocity VC and acceleration AC commands are not shown or used in this simplified example, but their use is contemplated for a more sophisticated controller, such as described in commonly owned U.S. patent application Ser. No. 11/509,172 entitled "Robotic Surgical System with Joint Motion Controller Adapted to Reduce Instrument Tip Vibrations," filed Aug. 24, 2006, which is incorporated herein by this reference.

A feedforward path (also referred to herein as a "feedforward controller") extends from the QC command to node 584 including blocks 550 and 552. Block 550 preferably includes logic for reducing internally generated frictional and inertial resistance when manually moving the slave manipulator, such as described in commonly owned U.S. patent application Ser. No. 11/479,144 entitled "Control System for Reducing Internally Generated Frictional and Inertial Resistance to Manual Positioning of a Surgical Manipulator," filed Jun. 30, 2006, which is incorporated herein by this reference. Block 552 is a torque limiting function that limits the torque command from the feedforward path to a maximum torque value MAXTRQ.

A feedback path (also referred to herein as a "feedback controller") includes sliding surface, integral and derivative paths extending from node 570 to node 582. The sliding surface path includes block 510 which is preferably a Sliding Surface (SS) function such as used in sliding mode control applications, block 511 which is a gain KP, and block 512 which is a limiter that limits the output of the sliding surface path to a torque value of PMAX. The integral path includes block 520 which is an input limiter which limits the magnitude of the position error that is to be processed through the path, block 521 which is an integrator gain KI, block 522 which is a limiter that limits the output of the integrator path to a torque value of IMAX, and block 523 which stores the prior output $Z_{-1}$ of the integrator path which is to be summed with a new output Z at node 585 to perform the digital integrator function. The derivative path includes block 530 which is a derivative function that generates a derivative of the position error QE to generate a velocity error VE, and block 531 is a derivative path gain KD.

Block 532 is a limiter that limits the output of the combined sliding surface and derivative paths to a torque value of PDMAX. The sequence of the two saturations PMAX and PDMAX is referred to herein as "cascaded saturation". When limiter block 512 has saturated (i.e., reached its limit) while limiter block 532 is not saturated (i.e., hasn't reached its limit), the resulting torque command is:

$$\tau_{PD} = PMAX + (\dot{Q}_C - \dot{Q}_S) \cdot KD \quad (2)$$

where $\tau_{PD}$ is the torque command contribution generated at node 581, PMAX is the saturated torque command contribution out of the limiter block 512, and $(\dot{Q}_C - \dot{Q}_S)$ is the velocity error VE generated by the block 530 from the position error QE.

The joint motion dynamic equation may be expressed as follows:

$$M \cdot \ddot{Q}_J = \tau_J \quad (3)$$

where "M" is a generic inertial parameter which is generally a function of the robot configuration, and $\tau_J$ is the total torque on the joint.

If we assume that $\dot{Q}_C = 0$, $\tau_{PD} = \tau_J$, $\dot{Q}_S$ is a displacement caused by a temporarily applied external force, then by substituting equation (3) into equation (2) and using the Laplace variable "s" to indicate the derivative operator, the joint velocity error is equal to the following:

$$\dot{q} = \frac{PMAX}{Ms + KD} \quad (4)$$

where $\dot{q} = \dot{Q}_S$ under the above assumptions.

At steady state, i.e. when the arm is not accelerating, it can be easily seen that the steady-state joint return velocity error "$\dot{q}_{SS}$" becomes:

$$\dot{q}_{SS} = \frac{PMAX}{KD} \quad (5)$$

Thus a constant steady-state return velocity error may be programmed by proper selection of PMAX and KD to prevent the joint from responding too quickly or slowly after a joint has been displaced due to a temporarily applied external force.

Figure 6:
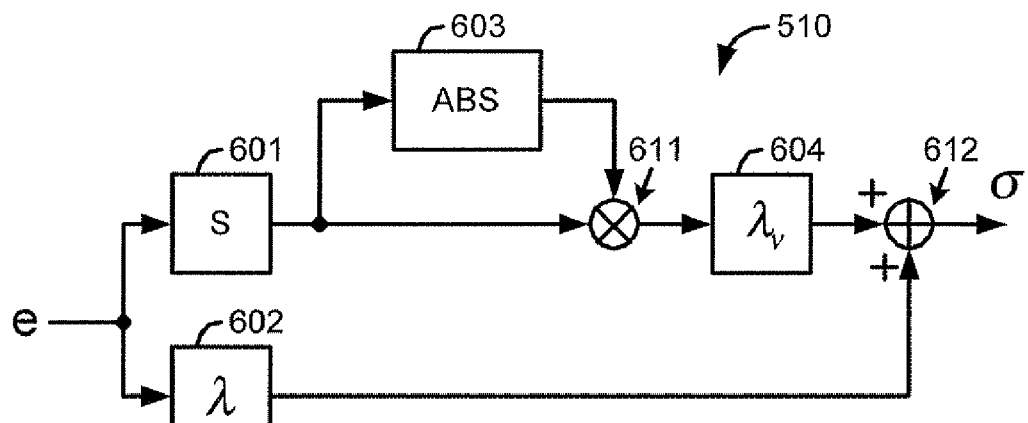
FIG. 6 illustrates a block diagram of a sliding mode surface function included in the slave feedforward and feedback controller with gravity compensation utilizing aspects of the present invention.

An example of the Sliding Surface block 510 is shown in FIG. 6, wherein the Sliding Surface is defined by the following:

$$\sigma = \lambda \cdot e + \lambda_v \cdot \dot{e}^2 \cdot \text{sgn}(\dot{e}) \quad (6)$$

where "$\sigma$" is the distance "SG" to the Sliding Surface (as defined by the relationship on the right as a function of "e" and "$\dot{e}$"), "e" is the position error (QC−QS), "$\dot{e}$" is the derivative of the position error (referred to herein as the "velocity error"), "sgn" is the well-known mathematical signum function, "$\lambda$" and "$\lambda_{98}$" are selected constants.

Given a sufficiently high gain KP for block 511, and while the PMAX limiter block 512 and the PDMAX limiter block 532 are not saturated, the feedback controller effectively keeps the joint on the Sliding Surface, so that $\sigma=0$, and equation (6) reduces to:

$$e = \frac{\lambda_V}{\lambda} \cdot \dot{e}^2 \cdot \text{sgn}(\dot{e}) \quad (7)$$

From equation (7), it derives that:

$$|\ddot{e}| = \text{constant} = a_{max} \quad (8)$$

as it can be verified by integrating twice equation (8) after eliminating the absolute value by assuming a positive acceleration to obtain the following basic velocity and position equations:

$$\dot{e} = a_{max} \cdot t + v_0 \quad (9)$$

$$e = \frac{a_{max}}{2} \cdot t^2 + v_0 \cdot t + x_0 \quad (10)$$

where t is the time variable.

By substitution of equations (9) and (10) into equation (8), the value of "$a_{max}$" may then be determined to be:

$$a_{max} = \frac{\lambda}{2 \cdot \lambda_V} \quad (11)$$

and consequently, the joint experiences a constant acceleration (referred to herein as "$a_{max}$") under the non-saturated conditions described above. Similarly by integrating twice equation (8) after eliminating the absolute value by assuming a negative acceleration, i.e. a deceleration, it can be shown that the joint experiences a constant deceleration (referred to herein as "$-a_{max}$") under the non-saturated conditions described above.

Thus, characteristics of the joint return trajectory (e.g., its acceleration/deceleration and steady state return velocity) are programmable by appropriately selecting parameters of the slave feedforward and feedback controller. By proper programming, a user-comfortable steady-state return velocity can be achieved as well as a user-comfortable acceleration/deceleration that avoids surprising human operators/users while reasonably returning the joint (and consequently, the slave manipulator) to its set point without the appearance of excessive delay when the medical robot has been displaced by a large amount from its set point, for instance to make temporary room for an assistant surgeon to access the surgical field. Further, the addition of the Sliding Surface function serves to prevent over-shoot past the set point, which is intrinsically less safe behavior for a slave manipulator in a medical robotic system. It can be appreciated that the user comfortable return velocities and accelerations are resulting from the mathematical properties of the described control scheme and from the chosen values for its parameters, hence the simplicity and robustness of the proposed approach as compared to alternative methods to achieve the same results, such as planning in advance the return trajectory, which then needs to be updated at discrete intervals of time and therefore, is considered to be a less desirable approach.

Figure 7:
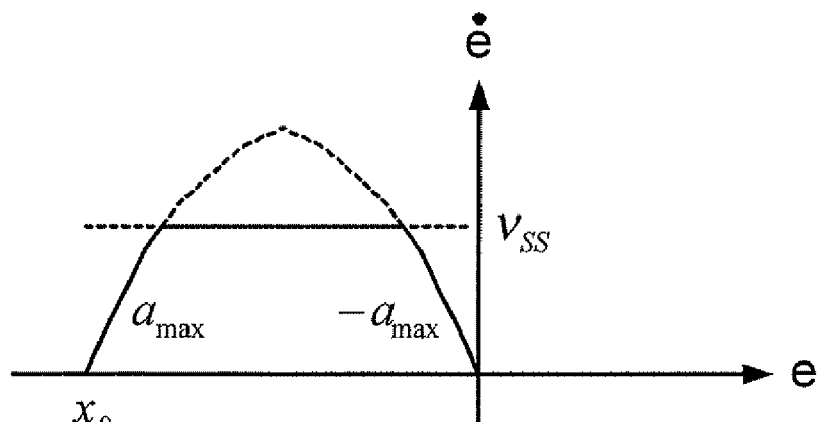
FIG. 7 illustrates a state-space diagram for the sliding surface function included in the slave feedforward and feedback controller with gravity compensation utilizing aspects of the present invention.

A convenient way of viewing the trajectory in this case is the state plane of the joint tracking error (e, ė), as illustrated in FIG. 7. As shown therein, when the limiter block 512 is saturated at PMAX, the steady-state velocity error $V_{SS}$ of the slave joint 580 is controlled to be equal to PMAX/KD per equation (5). On the other hand, when the limiter block 512 is not saturated, the acceleration error of the slave joint 580 is controlled to be equal to a maximum acceleration error "$a_{max}$" per equation (11) between the period in which the slave joint 580 has been displaced by an external force to a initial displacement of X0 (which is large enough to cause a threshold position error to be met) and until the limiter block 512 saturates, and the deceleration of the slave joint 580 is controlled to be equal to a maximum deceleration error of "$-a_{max}$" per equation (11) between the period in which the limiter block 512 is transitioning out of saturation and until the slave joint 580 returns to its target position or set point at the axes intersection.

Note that if a proportional function such as in the following equation (12) is used in the Sliding Surface block 510 instead of the quadratic function of equation (6):

$$\sigma = \lambda \cdot e + \lambda_v \cdot \dot{e} \quad (12)$$

then the steady-state velocity error $\dot{q}_{SS}$ will still be constrained according to equation (5). The joint acceleration error $a_{max}$, however, will not be constrained in this case according to equation (11). In such case, the return trajectory will either be overdamped to critically damped and hence very slow or tend to have a considerable overshoot when compared to the case making use of equation (11). It can also be appreciated that the return trajectory in FIG. 7 is the minimum time trajectory given limits on the velocity error and acceleration error.

A gravity compensation control system 540 receives information of sensed joint positions for all active joints of the slave manipulator 128 including the position QS of the joint 580, and generates appropriate torque commands for their respective motors to compensate for any gravity imbalance that may occur during movement of the slave manipulator 128. Details of one such a gravity compensation control system are provided in previously incorporated by reference and commonly owned, U.S. patent application Ser. No. 11/479,144. Other known gravity compensation control systems may also be used. Block 542 receives the output of the gravity compensation control system 540 to be provided to the motor joint 580 and limits it to a torque value of GCMAX.

Block 572 is a torque limiting function that limits the torque command from the feedback path to a maximum torque value MAXTRQ. Block 560 is a sensor feedback gain FBK which nominally has a value of one in the present example. Although shown as a sensor feedback gain, in the more sophisticated implementation of a joint controller as shown in FIG. 4, a joint observer may be used to generate not only an observed joint position, but also observed joint velocity and acceleration for feedback to a slave feedforward and feedback controller incorporating the various aspects of the present invention.

Figure 8:
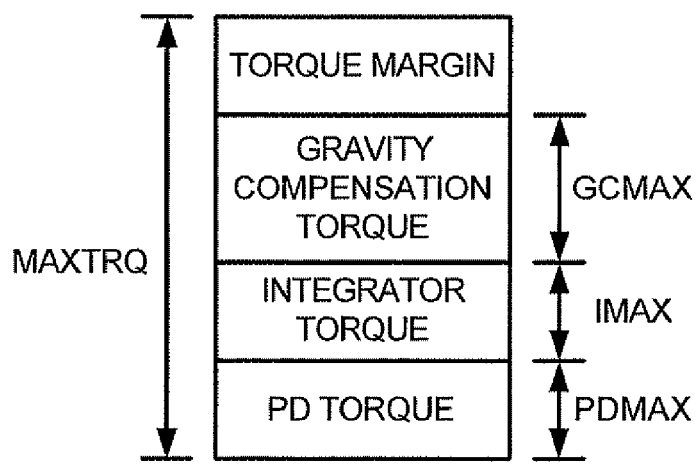
FIG. 8 illustrates a diagram of a torque budgeting scheme used in a joint controller utilizing aspects of the present invention.

In addition to cascaded saturation, torque budgeting is also employed in the slave feedforward and feedback controller, such as shown, for example, in FIG. 8. As shown therein, the maximum commmandable torque value MAXTRQ is budgeted between the gravity compensation torque command, which is limited to GCMAX, the integrator path torque command, which is limited to IMAX, and the combined proportional and derivative path torque command, which is limited to PDMAX. An extra torque margin is also budgeted in to accommodate feedforward path and control transients.

Although the various aspects of the present invention have been described with respect to a preferred embodiment, it will be understood that the invention is entitled to full protection within the full scope of the appended claims.

We claim:

1. A medical robotic system comprising:
   a manipulator having a motor driven joint for moving the manipulator; and
   a processor configured to control movement of the joint from a current position to a target position according to a control law from which a motor joint command may be determined using joint feedback and feedforward motor torque terms and a gravity compensation joint motor torque term, wherein the joint feedback motor torque term is computed as a function of at least a position error computed as a difference of the current and target positions, the feedforward joint motor torque term is computed as a function of the joint target position, the feedback motor torque term is limited to a first programmable limit value, the feedforward motor torque term is limited to a maximum motor torque value, and the gravity compensation joint motor torque term is computed as a function of at least the current position.

2. The medical robotic system according to claim 1, wherein the joint feedback motor torque term is computed as a function of the position error and a velocity error equal to a derivative of the position error.

3. The medical robotic system according to claim 1, wherein the feedforward joint motor torque term is computed as a function of the target position and a target velocity equal to a derivative of the target position.

4. The medical robotic system according to claim 1, wherein the feedforward joint motor torque term is computed as a function of the target position, a target velocity equal to a derivative of the target position, and a target acceleration equal to a derivative of the target velocity.

5. A medical robotic system comprising:
   a manipulator having a motor driven joint for moving the manipulator; and
   a processor configured to control movement of the joint from a current position to a target position according to a control law from which a motor joint command may be determined using joint feedback and feedforward motor torque terms, wherein the joint feedback motor torque term is computed as a function of at least a position error computed as a difference of the current and target positions and a velocity error computed as a derivative of the position error, the feedforward joint motor torque term is computed as a function of the target position, the feedback motor torque term is limited to a first programmable limit value the feedforward motor torque term is limited to a maximum motor torque value, the function used to compute the joint feedback motor torque term including first and second contributions respectively from first and second processing paths in response to at least the position error and velocity error, the first contribution limited to a programmable limit value, the second contribution generated by multiplying the velocity error by a programmable gain, and wherein the joint feedback motor torque term serves to prevent the current velocity error of the joint movement to exceed in absolute value a programmable maximum velocity error value that is determined by the ratio of the programmable limit value to the programmable gain.

6. The medical robotic system according to claim 5, wherein the joint feedback motor torque term is computed as a function of the position error and the velocity error, and serves to constrain the absolute value of the acceleration/deceleration error to a programmable maximum acceleration error value as long as the absolute value of the velocity error is not being limited to the programmable maximum velocity error value.

7. The medical robotic system according to claim 6, wherein the joint feedback motor torque term is computed as a function including a contribution calculated by summing first and second products, the first product calculated by multiplying the position error by a first programmable constant, the second product calculated by multiplying a square of the velocity error by a second programmable constant, and the programmable maximum acceleration error value is determined by half of the ratio of the first programmable constant to the second programmable constant.

8. A medical robotic system comprising:
a manipulator having a motor driven joint for moving the manipulator; and
a processor configured to control movement of the joint from a current position to a target position according to a feedback control law that computes the motor joint command as a function of the difference between the position and the target position and as a function of the difference between a current velocity and target velocity while preventing the current velocity error of the joint movement to exceed in absolute value a programmable maximum velocity error value, wherein the joint torque command is generated so as to include first and second contributions respectively from first and second processing paths in response to a difference of the current and target positions, the first contribution limited to a programmable limit value, the second contribution generated by multiplying a derivative of the difference by a programmable gain, and the programmable maximum velocity error value is determined by the ratio of the programmable limit value to the programmable gain.

9. A medical robotic system comprising:
a manipulator having a motor driven joint for moving the manipulator; and
a processor configured to control movement of the joint from a current position to a target position according to a feedback control law that computes the motor joint command as a function of the difference between the current position and the target position and as a function of the difference between a current velocity and target velocity while preventing the current velocity error of the joint movement to exceed in absolute value a programmable maximum velocity error value, wherein the processor is further configured to control movement of the joint by constraining the absolute value of an acceleration/deceleration error of the joint movement to a programmable maximum acceleration error value as long as the joint movement is not being limited to the programmable maximum velocity error value.

10. The medical robotic system according to claim 9, wherein the processor generates a joint torque command including a contribution calculated by summing first and second products, the first product calculated by a difference of the current and target positions multiplied by a first programmable constant, the second product calculated by a square of a first derivative of the difference multiplied by a second programmable constant, and the programmable maximum acceleration error value is equal to one-half of a quotient calculated by dividing the first programmable constant by the second programmable constant.

11. A method for controlling movement of a motor driven joint of a manipulator, comprising;
controlling movement of the joint from a current position to a target position according to a feedback control law that computes the motor joint command as a function of the difference between the current position and the target position and as a function of the difference between a current velocity and target velocity while preventing the current velocity error of the joint movement to exceed in absolute value a programmable maximum velocity error value.
wherein the controlling movement of the joint comprises:
generating a joint torque command including first and second contributions respectively from first and second processing paths in response to a difference of the current and target positions, wherein the first contribution is limited to a programmable limit value, the second contribution is generated by multiplying a derivative of the difference by a programmable gain, and the programmable maximum velocity error value is determined by the ratio of the programmable limit value to the programmable gain.

12. A method for controlling movement of a motor driven joint of a manipulator, comprising:
controlling movement of the joint from a current position to a target position according to a feedback control law that computes the motor joint command as a function of the difference between the current position and the target position and as a function of the difference between a current velocity and target velocity while preventing the current velocity error of the joint movement to exceed in absolute value a programmable maximum velocity error value; and
constraining the absolute value of an acceleration/deceleration error of the joint movement to a programmable maximum acceleration error value as long as the joint movement is not being limited to the programmable maximum velocity error value.

13. The method according to claim 12, wherein the constraining of the acceleration of the joint movement comprises: generating a joint torque command including a contribution calculated by summing first and second products, the first product calculated by a difference of the current and target positions multiplied by a first programmable constant, and the second product calculated by a square of a first derivative of the difference multiplied by a second programmable constant; and calculating the programmable maximum acceleration error value by calculating a quotient by dividing the first programmable constant by the second programmable constant, and multiplying the quotient by one half.

* * * * *